United States Patent [19]

Cathcart

[11] Patent Number: 4,849,507

[45] Date of Patent: Jul. 18, 1989

[54] HUMAN SUPPRESSOR FACTOR

[76] Inventor: Martha K. Cathcart, 2917 North Park Blvd., Cleveland Hts., Cleveland, Ohio 44118

[21] Appl. No.: 835,051

[22] Filed: Feb. 28, 1986

[51] Int. Cl.⁴ ............................................. C07G 7/00
[52] U.S. Cl. .................................... 530/351; 435/68; 436/501; 436/506; 436/536; 436/547
[58] Field of Search ................... 435/68; 436/501, 506, 436/536, 547; 530/351

[56] References Cited

U.S. PATENT DOCUMENTS 4,537,712  8/1985  Oh ..................................... 530/413 X
4,665,021  5/1987  Schnaper et al. .................. 435/68 X
4,665,032  5/1987  Laureuce ........................... 435/68 X

FOREIGN PATENT DOCUMENTS 0163218  12/1985  European Pat. Off. .

OTHER PUBLICATIONS

Krakauer et al., "Suppression of Polyclonel Immonoglobelin Biosynthesis . . .", Immunology 40, 53–60 (1980).

Primary Examiner—Robert J. Warden
Assistant Examiner—Richard Wagner

[57] ABSTRACT

A compound essentially free of compounds of molecular weight above 10,000, the compound characterized in that it is water soluble, it has a molecular weight between about 1,000 and 10,000, it suppresses immunoglobulin synthesis in pokeweed mitogen-stimulated human lymphocytes, it does not inhibit proliferation of human lymphocytes induced by concanavalin A or pokeweed mitogen, it inhibits phytohemmaglutinin-induced proliferation of human T4 cells, and it inhibits IL-2 production of human T4 cells.

1 Claim, 7 Drawing Sheets

HUMAN SUPPRESSOR FACTOR

BACKGROUND OF THE INVENTION

The application of cell hybridization technology to immunology by Kohler and Milstein has created revolutionary changes in strategy in investigations in the area of immunology. Although this technology was first applied to obtain monoclonal antibodies against predefined antigens in the murine B lymphocyte system, it recently has been employed to investigate immunoregulatory molecules in the T lymphocyte system. Most laboratories attempting to establish lymphokine secreting T cell hybridomas have used activated or sensitized T cells, which can be obtained by stimulating lymphocytes with mitogenic lectins or antigens. Pathologic lymphocytes can also provide a useful source of valuable immunoregulatory mediators. For example, T cells or thymocytes from patients with immunodeficiency diseases associated with hypo- or agammaglobulinemia may provide a lymphokine source for investigating the abnormalities of immunoregulation and may also provide information on mechanisms involved in normal immunoregulation.

Common variable hypogammaglobulinemia (CVH) is a late onset acquired immunodeficiency disease having the typical feature of significantly reduced levels of all classes of immunoglobulin. Patients with this disease have an increased incidence of sinorespiratory infection such as acute and chronic sinusitis, chronic bronchitis, bronchiectasia and interstitial pneumonia which sometimes cause septicemia. Patients also may have abnormalities of cellular immunity as assessed, by negative delayed hypersensitivity skin tests or depressed responses of peripheral blood lymphocytes to PHA. These patients are prone to produce autoantibodies. This is a paradoxical phenomenon, however, and autoimmune diseases occur with a much greater incidence than in normal individuals. The incidence of CVH with associated thymoma is reported to be about 10%, and about 10% of the cases manifest pure red cell aplasia which is thought to be due to IgG antibody against erythroid stem cells. The pathogenesis of CVH has not been clearly understood, but it has been suggested that suppressor T cells inhibit the maturation of B lymphocytes into antibody secreting plasma cells.

SUMMARY OF THE INVENTION

In general, the invention features a compound (a suppressor factor) essentially free of compounds of molecular weight above 10,000, the compound being characterized in that it is water soluble, it has a molecular weight between about 1,000 and 10,000, it suppresses immunoglobulin synthesis in pokeweed mitogen-stimulated human lymphocytes, it does not inhibit proliferation of human lymphocytes induced by concanavalin A or pokeweed mitogen, it inhibits phytohemmaglutinin-induced proliferation of human T4 cells, and it inhibits IL-2 production of human T4 cells.

The unique combination of features of the suppressor factor of the invention—particularly its antibody and IL-2 inhibitory capacity combined with its failure to inhibit the proliferation of non-target cells—renders the suppressor factor useful in a number of therapeutic and diagnostic applications. In therapy in particular, the failure of the factor to affect most cells of the immune system allows its use without the risk of generalized damage to or suppression of the immune system. The uses of the factor, and its properties and advantages, are described in detail below, and other features and advantages are within the claims.

DESCRIPTION OF THE PREFERRED EMBODIMENTS

The drawings are first described.

Drawings

FIG. 1 is a pair of graphs illustrating the suppression of IgM synthesis by supernatants of five hybridoma clones and a control tumor line.

FIG. 2 is a pair of graphs illustrating: (A) the time course of pokeweed mitogen stimulated IgM synthesis and the effect of the suppressor factor of the invention in the clone 8E-24 supernatant on such synthesis; numbers in parenthesis indicate percent suppression of IgM production as compared to control media; (B) the lack of effect of the suppressor factor on pokeweed mitogen induced cell proliferation.

Figure 5:
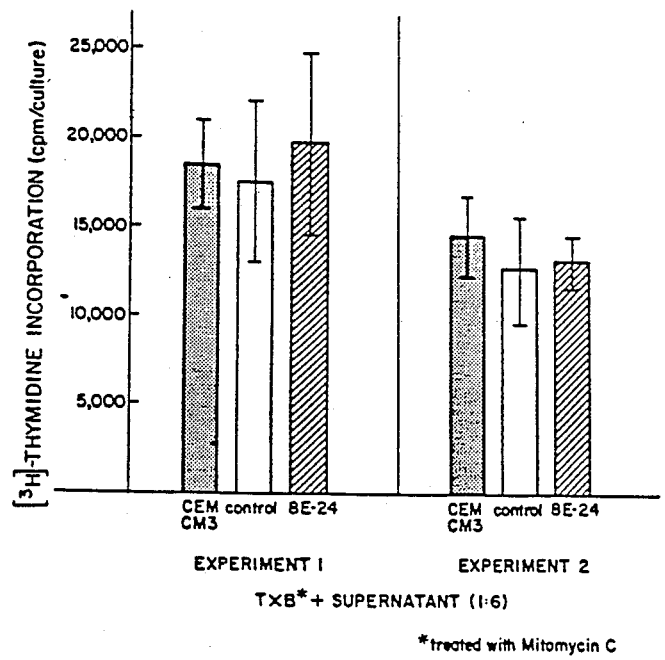

FIG. 5 is a graph illustrating the effects of hybridoma supernatants on mixed lymphocyte cultures (MLC). Equal number of T lymphocytes (T) and mitomycin-C treated allogeneic B lymphocytes (B*) were incubated. Cells were pulsed with 0.5 $\mu$Ci/well of [$^3$]-thymidine six hours prior to harvesting in the five day culture period.

Figure 6:
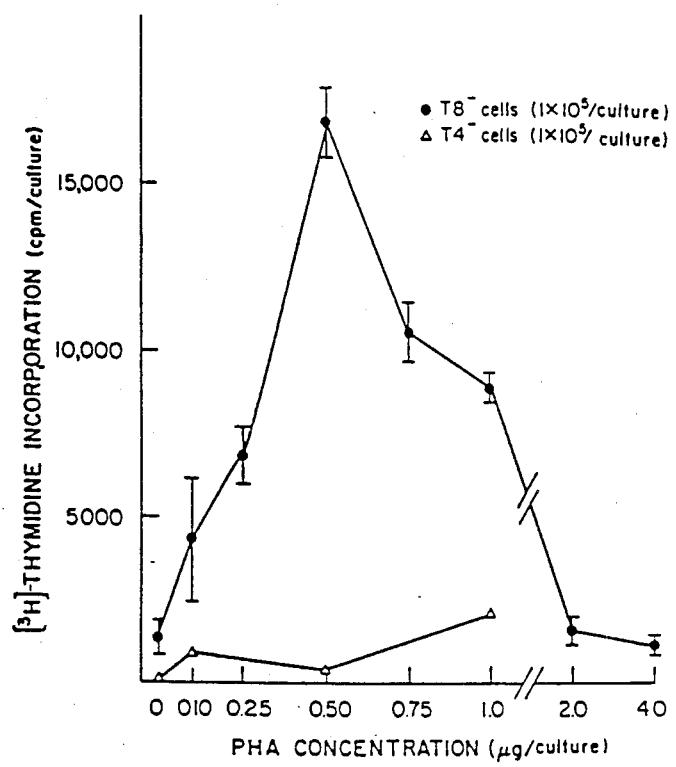

FIG. 6 is a graph illustrating the PHA responsiveness of T cell subsets.

Figure 7:
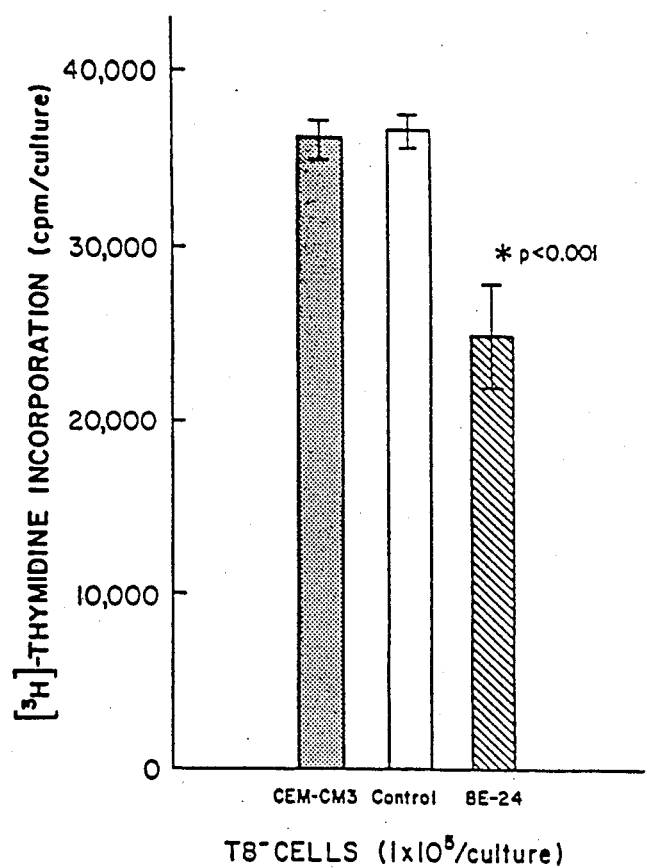

FIG. 7 is a graph illustrating the effect of hybridoma supernatants on T8$^-$proliferation in response to PHA; $1 \times 10^5$ T8$^-$cells were exposed to 0.5 $\mu$g PHA for three days with or without the addition of hybridoma 8E-24 supernatant. 0.5 $\mu$Ci/well [$^3$H]-thymidine was added six hours prior to harvesting.

Hybridoma Cell Line

Hybridoma cell line 8E-24 was formed by fusing thymus cells from a patient with CVH and thymoma to a human T cell tumor line, as follows.

Thymus Cells and Cell Line

Thymus issue was obtained from a 64 year old male patient with common variable hypogammabulinemia, invasive thymoma, and pure red cell aplasia. The thymus was surgically removed for therapeutic reasons.

There has been previously described an HGPRT (hypoxanthineguanine phosphoribosyl transferase) deficient human T cell line, CEM-CM2 (Cathcart, M. K., and Murakami, M., In "T Cell Hybridomas" (M. J. Taussig, Ed.) (in press) CRC Press, Inc., Boca Raton, Fla., 1984).

This line was subsequently cloned by limiting dilution. Clones growing rapidly in the presence of Interleukin 2 (IL- 2, BRL. Gaithersburg, Md.) were obtained. The clone termed CEM-CM3 was utilized in these studies and was determined to be 100% sensitive to aminopterin at a concentration of $2 \times 10^{-7}$M, the concentration used for the HAT selection medium (RPMI with hypoxanthine-aminopterin-thymidine). CEM-CM3 has been deposited in the American Type Culture Collection (Rockville, Md.) for distribution. CEM-CM3 was found to be free of mycoplasma by both direct assay by cultivation and indirect assay by DNA staining with Hoechst stain as performed by the American Type Culture Collection. This cell line was routinely maintained with 15 μg/ml 8-azaguanine.

Cell Fusion Procedure

Cell fusion was performed according to a modified version of the procedure described by Galfre and Milstein In "Methods of Enzymology", Vol. 73 (J. J. Langone and H. Van Vunakis, Eds) pp. 3–46, Academic Press, New York, 1981. Briefly, $5 \times 10^6$ viable thymus cells and $5 \times 10^6$ CEM-CM3 cells, taken from log-phase cultures, were mixed together and pelleted by centrifugation at $200 \times G$ for 10 minutes. 0.5 ml of 50% polyethylene glycol (molecular weight 1500 BDH Chemical LTD., England) in RPMI 1640 was added to this pellet at room temperature and left for 2 minutes. The suspension was gradually diluted to 12 ml with RPMI over a period of 3 minutes, and then pelleted by centrifugation at $200 \times G$ for 5 minutes. The cells were gently resuspended in 10 ml of RPMI 1640 containing 100 IU/ml penicillin, 100 μg/ml streptomycin, 2 mM glutamine, 10 mM Hepes buffer and 15% heat inactivated fetal calf serum (FCS-RPMI), and then plated in 96 well flat bottomed plates. Selective HAT medium (hypozanthine $1 \times 10^{-4}$M, aminopterin $2 \times 10^{-7}$M, thymidine $1.6 \times 10^{-5}$M, and 15% FCS-RPMI) was added on days 1,2,3,6,9 and 12 after fusion, and then replaced by HT medium (hypoxanthine, thymidine) for 7 days. Cultures were incubated in a humidified atmosphere of 10% $CO_2$ and 90% air at 37° C. Microscopic cell growth was observed on the 10th day in two of the microtiter wells (8C and 8E). Eight to ten weeks after cell fusion, limiting dilution cloning was performed and cultures were included in the presence of 25% IL-2. Twenty four clones were derived from 8E and thirteen clones from 8C at a plating dilution of one cell per well and one cell per two wells.

Screening Assay for Suppressive Activity

Supernatants from cultures of cloned cells (13 clones from 8C and 24 clones from 8E) were tested for their ability to suppress in vitro IgM production. This assay was used as a screening procedure by adding a final 1:6 dilution of hybrid clone supernatants or medium to $3 \times 10^5$ peripheral blood mononuclear cells (PBMC) per microtiter well (u-bottom, 96 well plates) in 10% FCS-RPMI with pokeweed mitogen (PWM) at a predetermined optimal dose for antibody synthesis (final dilution 1:1000). The PBMC were obtained from normal donors by density centrifugation, and platelets were removed by passing the cells twice through IM sucrose gradients. These cultures were incubated for 7 days at 37° C. in a humidified atmosphere with 10% $CO_2$, and 90% air. The culture supernatants were then collected and assayed for IgM by a solid phase immunofluorescent assay utilizing purified human serum IgM as a standard.

IgM Quantitiation.

Figure 1:
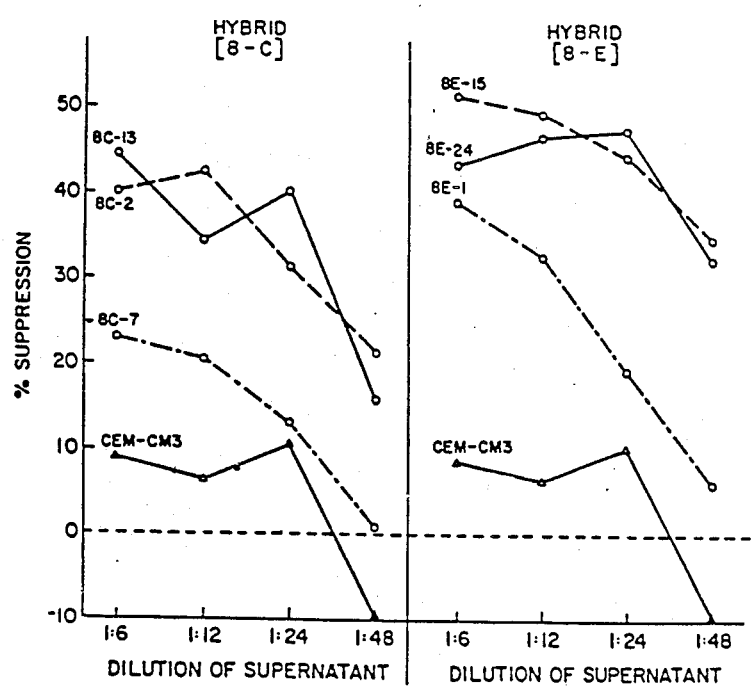

To estimate the quantity of IgM in culture supernatants, the solid phase immunofluorescent assay was used according to the method described in Cathcart et al., id. Briefly, 200 μl of a culture supernatant were incubated for 90 minutes with 0.75 ml (1 mg/ml) polyacrylamide beads coated with rabbit antihuman IgM antibody (Bio. Rad. Laboratories, Richamond, Calif.). 0.15 ml flourescein-conjugated goat anti-human IgM (0.1 mg/ml specific antibody, Litton Bionetics, Charleston, S.C.) was then added. After incubating for an additional 60 minutes, the beads and bound material were washed twice with phosphate buffered saline (PBS) by centrifugation at $400 \times G$ for 5 minutes. The beads were resuspended in 2 ml of PBS and the flourescence was measured on a Bio. Rad. automated fluorometer. The results for a few selected clones are given in FIG. 1; data are expressed as nanograms of IgM per culture as compared to a standard curve using purified human serum IgM (Meloy, Springfield, Va.). As is shown in FIG. 1, supernatants from several clones showed 40-60% suppression in the screening assay at a dilution of 1:6. These clones were cultured in RPMI 1640 without FCS at $4 \times 10^6$/ml for two days and the supernatants were evaluated for suppressive activity. 8E-24, which was cloned by limiting dilution at 0.5 cells per well, displayed more than 40% suppression at a 1:6 to 1:24 dilution and more than 30% suppressive activity still remained at a 1:48 dilution. 8E-1 and 8C-7 which were grown from wells originally seeded with 1 cell per well lost their suppressive activity at a 1:48 dilution. Supernatants from the parental cell line CEM-CM3 also showed a low level of suppression on activity, but not nearly as much as the hybrid supernatants. This is a consistent finding with this line. Since 8E-24 was derived from a limiting dilution plating at 0.5 cell/well and therefore was most likely derived from a single cell, and it consistently showed significant suppressive activity, this clone was used for further studies. As is shown in FIG. 1, the suppressor factor of the invention was produced not just by 8E-24, but also by other clones, most notably 8C-13, 8C-2, 8E-15, and 8E-1. In addition, to obtain other hybridoma clones producing the suppressor factor of the invention, thymus cells of a patient with CVH can be fused to a human T cell tumor line and the supernatants screened for suppressor activity as described above.

To determine the rate of proliferation of the 8E-24 cells as compared to their parental CEM-CM3 cell line, 24 and 48 hour cultures were evaluated for [$^3$H]-thymidine incorporation and total cell protein levels (by the method of Lowry et al.). In numerous experiments no significant differences were noted between the two lines.

Proliferation Assays

To examine the effect of hybridoma supernatants on the proliferative response of PBMC to various mitogens, $2 \times 10^5$ PBMC were cultured in u-bottomed wells of 96 well microtiter plates (Falcon) in the presence or absence of the hybridoma supernatants at a concentration of 1:6 and the following mitogens were added at previously determined optimal concentrations; phytohemmaglutinin (PHA 16 μ/ml), concanavalin A (Con A 4 μg/ml), lipopolysaccharide (LPS, *E. coli* 055:B5, 125 μg/ml) and PWM. For the LPS induced proliferation, PBMC were cultured in 10% human AB serum in RPMI as described by Miller et al. (1978) J. Immunol: 121, 2160. The cultures were pulsed with 0.5 μCi per well of [$^3$H]-thymidine (Schwarz/Mann, Spring Valley, N.Y.) six hours before harvesting. PHA and Con A stimulated cultures were harvested by filtration using a multiple sample harvester on the third day. LPS-stimulated cultures were harvested on the 9th day, and PWM on days one through seven. Following filtration and generous washing the glass fiber filters were dried, placed in scintillation vials with toluene containing 4 g/l Omnifluor (New England Nuclear, Boston, Mass.) and the radioactivity was measured on a Beckman LS7500 beta scintillation counter.

To study the effect of hybridoma supernatants on the mixed lymphocyte culture (MLC), T cells and non-T cells from two different individuals were obtained by a standard overnight rosetting procedure with SRBC. Non-T cells were treated with mitomycin C (50 μg/ml) at a concentration of $2\times10^6$ cells/ml for 30 minutes at 37° C. and washed extensively before being used as stimulator cells. $1\times10^5$ T cells and $1\times10^5$ allogeneic non-T cells were added together and incubated fo 5 days in the presence or absence of hybridoma supernatants. The cultures were pulsed with [$^3$H]-thymidine (0.5 μCi/well) six hours before harvesting. Thymidine incorporation was quantiated as described above.

To further examine the effect of hybridoma supernatants on PHA induced proliferation of T cells, T cells were separated into two groups by a plate separation method utilizing the monoclonal antibodies OKT4 and OKT8 (Ortho Diagnostic System Raritan, N.J.) (12). SRBC rosetted T cells ($1-2\times10^7$) were incubated with either a 1/25 dilution of OKT4 or a 1/200 dilution of OKT8 in 5% FCS-RPMI (in 0.65 ml and 2 ml volume respectively) on ice for 45 minutes with mixing every 15 minutes. The cells were then pelleted, and resuspended cells (in 2 ml of 5% FCS-RPMI) were added dropwise to a plastic petri dish (6 cm in diameter, Lab-Tek, Miles Laboratories, Naperville, Ill.) previously coated with rabbit anti-mouse immunoglobulin (Ortho Diagnostic System, Raritan, N.J.) for one hour with a final concentration of 100 μg/ml diluted in 5 ml of 0.05 M Tris-saline. After incubating the plate at 4° C. for 70 minutes nonadherent cells were collected. The OKT8 nonadherent cells (T8$^-$) were used as an enriched population of T4$^+$ cells, and the OKT4 nonadherent cells (T4$^-$) were used as T8$^+$ cells. Purity of the negatively selected cell populations ranged from 88 to 97% as determined by an immunofluorescent OKT4 and OKT8 staining procedure and evaluation on a flourescence activated cell sorter (Becton-Dickinson FACS II). The PHA responsiveness of T8$^-$ and T4$^-$ cells ($1\times10^5$) at a previously determined optimum concentration of PHA (0.5 μg/culture), was studied in the presence or absence of the 8E-24 supernatant.

Figure 2:
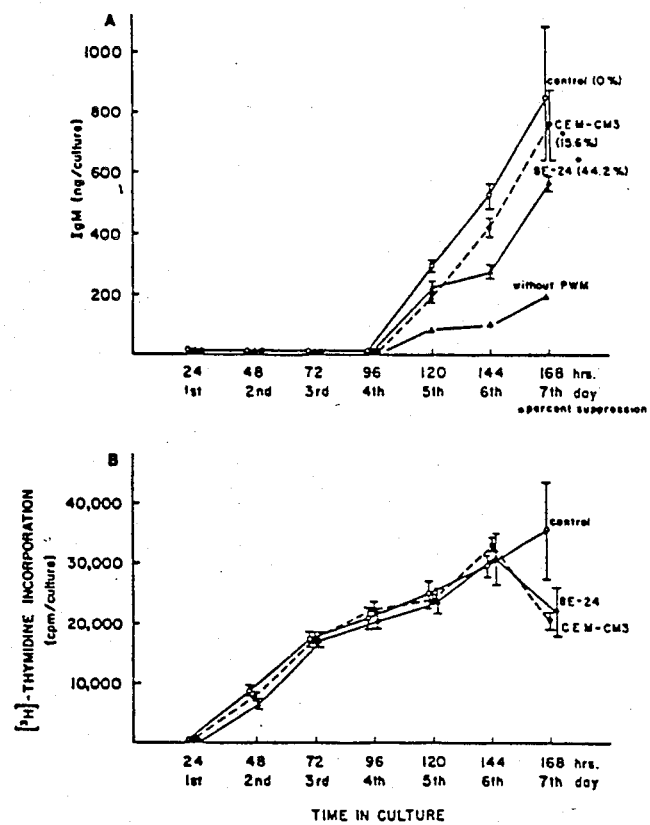
Figure 4:
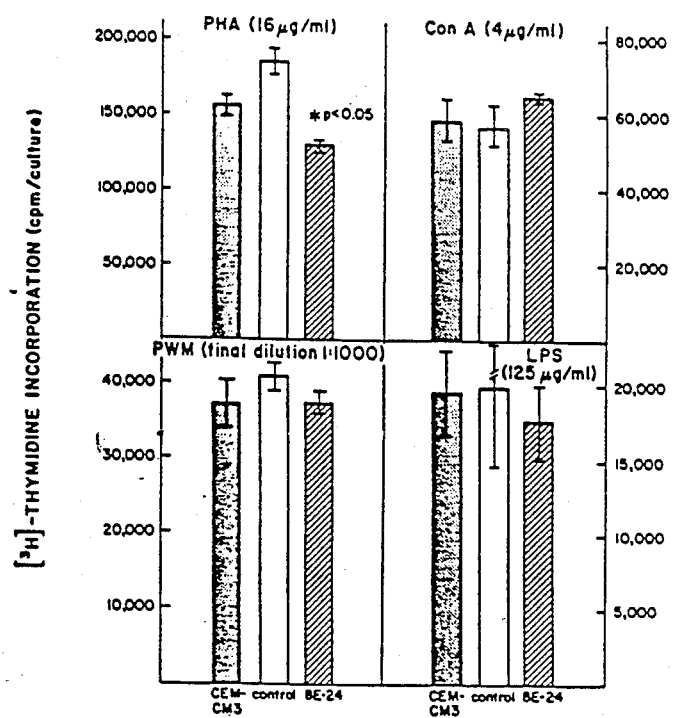
FIG. 4 is a graph illustrating the effect of hybridoma supernatants on proliferative responses. Cells were pulsed with 0.5 $\mu$Ci/well of [$^3$H]-thymidine six hours prior to harvesting in the three day (PHA, Con A, PWM), and nine day (LPS) culture periods.

As is shown in FIG. 2B, the PWM induced proliferative response was not inhibited by the hybridoma supernatant. As shown in FIG. 4, the 8E-24 supernatant also had no effect on PWM induced proliferation. It did not affect LPS- or Con A-induced proliferation but signficantly suppressed PHA responsiveness by 30–50% ($P<0.05$). The CEM-CM3 supernatant caused about 17% suppression but this was not signficantly different from the positive control cultures. As is shown in FIG. 5, no suppression was brought about by the 8E-24 supernatant in the MLC response.

It was determined that Con A stimulation does not modulate the suppressive activity of 8E-24 cells. The suppressive activity of supernatants from Con A-stimulated 8E-24 cells ($1\times10^5$ 8E-24 cells were stimulated with 4 μg/ml Con A for twenty four hours) revealed similar suppressive activity to that mediated by nonstimulated 8E-24 cells.

Characterization of Hybrid Cells

Analysis of the cell surface phenotype, HLA markers and karyotype were performed on the cloned hybrid 8E-24 cells and compared to the parental CEM-CM3 cells and patient thymus cells using monoclonal antibodies (Ortho, Raritan, N.J.) counterstained with a flourescein-conjugated antisera and evaluated on a flourescence activated cell sorter (Becton Dickinson, FACS II). The surface phenotypes of CEM-CM3 and 8E-24 were compared. More than 90% of both CEM-CM3 and 8E-24 cells displayed surface determinants recognized by OKT10 (a monoclonal antibody directed toward anti-human stem cells, thymocyte and null cell markers). 37.3% of CEM-CM3 cells revealed a T4 positive phenotype (human inducer/helper T cell marker), whereas 4.3% of 8E-24 cells positively stained OKT6 monoclonal antibody (anti-human thymocyte) reacted with 2.1% of 8E-24 cells, whereas 0.1% revealed positive staining in the CEM-CM3 cell population. Both CEM-CM3 and 8E-24 cells showed detectable but low levels of surface immunoglobulin staining.

HLA typing was determined for CEM-CM3, thymus cells and 8E-24 cells by microlymphocyte cytotoxicity testing using panels of alloantisera by the Tissue Typing Laboratory, Cleveland Clinic Foundation. Thymus cells from the patient expressed A1/AW19 and B8/14 alloantigens, while CEM-CM3 expressed A1/AW19, B14/40 and C7, and 8E-24 hybrid cells expressed A1-/AW10, B8/40 and C7. Because the patient died before peripheral blood typing was performed, these results were verified by investigating the peripheral blood lymphocytes from the patient's son, whose HLA type was determined to be A 1/11, B 8/35, C 7/4. Although the HLA markers expressed on these three cell samples were very similar, it is certain that the B8 antigen on 8E-24 hybrid cells was derived from the thymus cells.

Chromosome Analysis

Chromosome studies were performed about 4 months after the fusion by the Cytogenetics Laboratory of the Cleveland Clinic Foundation. Briefly, Colcemid (Gibco, Grand Island, N.Y.) was utilized to induce metaphase spreads, which were fixed with methanol/-glacial acetic acid. The cells were stained with Giemsa for microscopic examination.

The chromosomal analysis was performed about 4 months after the fusion. At this point 8E-24 cells showed no evidence of polyploidy and the modal chromosome number of 20 cells counted was 46 whereas CEM-CM3 cells showed 47 chromosomes. Since 5 cells of the 8E-24 cells showed less than 42 chromosomes and most 8E-24 cells presented monosomy X (whereas CEM-CM3 cells showed XX), it is obvious that 8E-24 cells lost many chromosomes of the parental cells following fusion, as observed by others.

Mechanism of Suppression

To determine the time course and mechanism of action of the hybrid supressor factor, several experimental approaches were utilized. First, the effect of the hybrid supernatants on lymphocyte proliferation during the antibody synthesis assay was examined. Quantitative measurements of IgM synthesis and [$^3$H]-thymidine incorporation by PWM stimulated PBMC were determined in replicate cultures at various times during the seven day incubation in the presence or absense of hybridoma supernatants. As shown in FIG. 2A, initial IgM production by PWM stimulated PBMC was first detectable on the fifth day of culture. Significant suppression of IgM synthesis by the 8E-24 supernatant was first observed on the sixth day (57.9% suppression) and continued to be detected on the seventh day (44.2%). Supernatants of the parental CEM-CM3 line also showed 15.6% suppression on day seven, but this was not significantly different from the media control. The initial proliferative response to PWM was observed on the second day of culture (FIG. 2B). No difference was seen between 8E-24. CEM-CM3 and control supernatant throuqh the sixth day. On day seven 8E-24 and CEM-CM3 supernatants showed similar suppression of proliferartion as compared to fresh medium. This similar drop is probably due to nutritional depletion in the supernatant cultures. No significant difference was observed between the parent cell and hybridoma cell supernatants in this regard. Therefore, the 8E-24 supernatant does not appear to affect antibody production through interference with the PWM induced proliferative response.

The effect of the supernatants on cell viability was also investigated in a similar culture system. There was no difference in cell viability (determined by Trypan blue exclusion upon microscopic examination) between cells exposed to the 8E-24 supernatant and control media throughout the seven days of culture. This indicates that suppression was not due to a selective cytotoxic effect.

Figure 3:
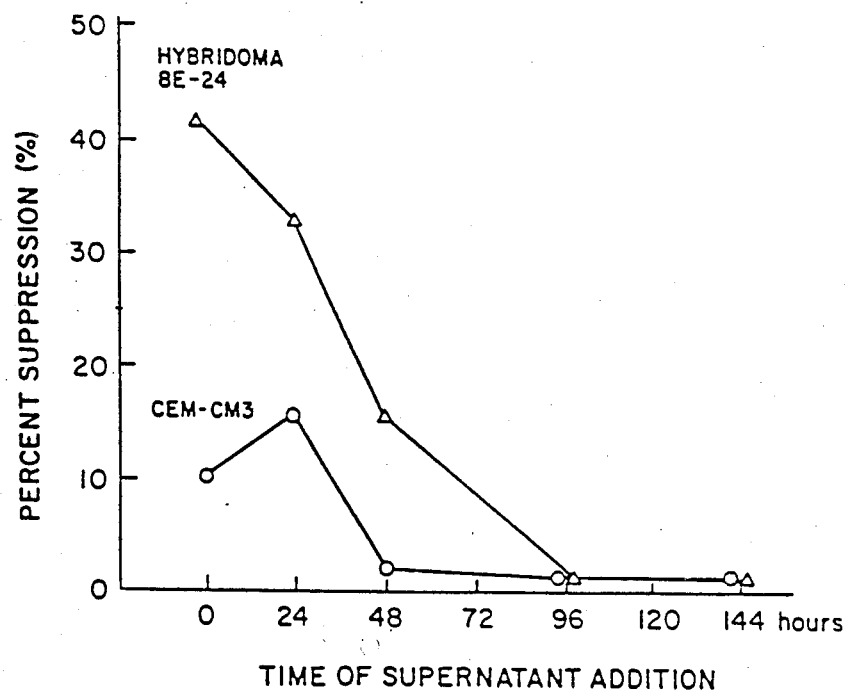
FIG. 3 is a graph illustrating the effects on IgM synthesis of the suppressor factor (8E-24 supernatant at a 1:6 dilution) at varying times after stimulation with pokeweed mitogen.

Experiments were performed to determine if suppression of antibody synthesis required early exposure to the suppressive supernatant. As shown in FIG. 3, the hybridoma supernatant had to be added to the culture within the initial forty eight hours to express its suppressive activity. The suppressive activity was not observed if the 8E-24 supernatants were added after the initial ninety six hours. Other experiments showed that this suppression was reversible (Table 1). PBMC were incubated with the hybridoma supernatant for 24 hours, 72 hours, and the full seven days. In hours 24 and 72 hours cultures the cells were washed twice and then control media containing PWM was added. As shown in Table 1, IgM production measured after 7 days in culture was suppressed if the suppressor factor was removed after 72 hours of incubation, whereas no suppression was observed when removed after 24 hours. These results suggest that cells must be exposed to the suppressor factor for more than 24 hours but less than 72 hours in order to realize the full suppressive effect.

Target Cells for Suppressive Activity

The above results suggest that a select population of T cells are the target cells of the suppressive activity exhibited by the hybrid supernatants. These findings were confirmed by evidence that this suppressive activity was abrogated by preincubating the hybridoma supernatants with purified T cells ($2 \times 10^7$/ml) for 2 hours (Table 3). To determine which population of T cells was affected, T cell subsets T8− (OKT8 nonadherent cells, predominantly T4+ cells) and T4− (OKT4 nonadherent cells, predominantly T8+) cells were prepared. As shown in FIG. 6, the T8− cells were the predominant subset responding to PHA induced proliferation in these cultures. Therefore, the effect of 8E-24 supernatnnts on T8−cell proliferation was studied. As shown FIG. 7, 8E-24 supernatants caused significant suppression (30% suppression, $P < 0.00$) of the PHA-induced proliferation of the T8− cell population. Further studies with the hybridoma supernatants showed that the highest suppression for IgM production in reconstructed cultures with T4+ cells and B cells at the ratio of 2:1. The degree of suppression could be reduced by increasing the ratio of T4+ cells (Table 4). These results provide further support that the immunosuppression mediated by this supernatant involves the T4+ cells as a target cell.

Molecular Size of the Hybridoma Suppressor Factor

To estimate the molecular size of the hybridoma suppressor factor, the hybridoma supernatants were separated into two fractions using a defined pore microconcentrator with an approximate 10,000 MW pore size (Centricon 10, Amicon, Danvers, Mass.). The majority of the suppressive activity was found in the supernatant after passing it through the filter (Table 5). No loss of potency of suppression of IgM synthesis was observed in this fraction, thus suggesting that the molecular size of the suppressor factor is less than 10,000 MW. A similar procedure established that the factor has a molecular wight above 1,000.

IL-2 Inhibition

It was observed that decreased PHA-induced proliferation of T4 cells was accompanied by a corresponding decrease in IL-2 production in those cells. Peak IL-2 production of PWM stimulated peripheral blood mononuclear cell cultures (occurring on the second day) was significantly suppressed by the 8E-24 supernatant, which had no effect on IL-1 production in these cells.

Use

The uses of the suppressor factor of the invention are based on its unique properties, most particularly its ability to target a subset of human T lymphocytes involved in regulating the synthesis of antibodies and in the production of IL-2, while leaving other components of the immune system unaffected. Uses fall into two main categories: diagnosis and therapy.

Diagnosis

Human Patients suffering from autoimmune diseases in which harmful antibodies circulate in the bloodstream will be expected to exhibit abnormally low blood levels of the suppressor factor of the invention. Assaying blood or other biological fluid samples for the factor can thus provide a means of monitoring therapy and assessing the immune status of patients with autoimmune diseases, e.g., systemic lupus erythematosis (SLE).

Such assays can be carried out by conventional immunoassay methods employing antibodies to the suppressor factor, made by conventional techniques in which a rabbit is immunized with the factor and the resulting antibody harvested and labeled, e.g., with a radioisotope.

Another non-therapeutic use of the supressor factor of the inventions in the dissection of human T cell populations into subsets based on reactivity with the factor. This can be carried out by the technique known as "panning", in which a substrate is coated with the factor and then washed with suspensions of T cells, only a fraction of which adhere to the coated substrate. This adhering fraction represents a subpopulation involved in antibody and IL-2 synthesis. The suppressor factor can also be labeled and used to assay blood samples for T cells of this subpopulation, to give an indication of the immune status of patients such as SLE patients, or to monitor events such as allograft rejection, which are likely to be preceded or accompanied by increased numbers of these suppressor-reactive cells.

Therapy

For use in therapy, the suppressor factor of the invention is first purified to homogeneity using conventional techniques. It can then be used therapeutically in at least two different ways: (1) to remedy a deficiency of the factor in patients such as SLE patients, and (2) to target and lyse the T cell subpopulation for which the factor is specific.

For treatment of suppressor factor deficiency, administration will preferably be intravenous, at a frequency of between once per day to once per month, most preferably about once per week. Amounts will be measured in activity units as is the case for lymphokines such as IL-2. Accordingly, one unit is defined as the amount of suppressor factor required to affect a 50% suppression of total IgM in $3 \times 10^5$ lymphocytes in a 100µ liter volume. In a typical human SLE patient, the goal is to achieve at least this level of suppression, to produce significant SLE symptom alleviation, thus requiring the administration of about 1 unit suppressor factor/ml, or 4,000–8,000 units per person, in a weekly injection. (8E-24 supernatant is of a concentration of about 10 units/ml.)

The T cells to which the suppressor factor of the invention binds are involved in the production of IL-2, and are thus likely to be involved in the rejection of allografts and in graft-versus-host disease, both of which are known to involve IL-2 producing activated T cells. For destruction of the deleterious T cell subpopulation in the treatment of these two conditions, the suppressor factor, which is not by itself lytic, must be coupled, using conventional techniques (see, for example, Bacha et al. U.S. Pat. No. 4,468,382, hereby incorporated by reference) to a cytotoxin such as ricin or diphtheria toxin. The resulting toxic conjugate is admixed with saline or any other suitable pharmaceutically acceptable carrier substance, and administered, e.g., intravenously, to kill the unwanted cells while sparing other cells to which the suppressor factor does not bind. This treatment can be used to inhibit the rejection of allografts, e.g., kidneys, and can also be used in the preparation, prior to transplantation, of lymphocyte-containing allografts such as bone marrow, to prevent graft-versus-host disease.

Other embodiments are within the follwing claims. For example, as mentioned previously, the suppressor factor is a natural product of certain human lymphocytes, and thus can be produced by any suitable human T-cell hybridoma. Once the factor has been further characterized chemically, it will probably be possible to produce it by means other than the culturing of hybridoma cells, e.g., by genetic engineering techniques. Additional therapeutic uses, e.g., the treatment of certain cancers in which IL-2 production may play a role, are also possible.

TABLE 1
EFFECTS OF SUPERNATANT REMOVAL ON SUPPRESSION OF IGM SYNTHESIS

| Time of Supernatant removal[b] | IgM Production in 7 day Cultures, ng/culture[a] | | |
|---|---|---|---|
| | Medium Control | Supernatants (1:6 dilution) | |
| | | CEM-CM3 | 8E-24 |
| After 24 hours | 286 ± 87(0)[c] | 277 ± 116(3) | 256 ± 85(11) |
| After 72 hours | 164 ± 40(0) | 134 ± 17(18) | 86 ± 24(48)[d] |
| No change | 205 ± 34(0) | 211 ± 17(0) | 134 ± 7(35)[d] |

[a] $3 \times 10^5$/well PBMC were incubated with PWM (1:1000) with or without hybridoma supernatants at a 1:6 dilution. The amount of IgM production was determined on day 7.
[b] Media was removed after 24 and 72 hours and the same amount of fresh media containing PWM was added.
[c] Data are expressed as mean ± S.D. of triplicate samples. Percent suppression is given in parentheses.
[d] Statistically significant from control media by student's t-test, $p < 0.05$

TABLE 2
EFFECTS OF ABSORPTION WITH T CELL AND B CELL POPULATION

| | Supernatants absorbed with[a] | IgM Production in 7 day Cultures, ng/culture | | |
|---|---|---|---|---|
| | | Medium Control | Supernatants (1:6) dilution | |
| | | | CEM-CM | 8E-24 |
| Expt. I | unabsorbed | 696 ± 90(0)[c] | | 324 ± 58(53) |
| | T cells[b] | 372 ± 40(0) | | 351 ± 118(6) |
| | B cells[b] | 255 ± 55(0) | | 129 ± 18(49) |
| Expt. II | unabsorbed | 677 ± 86(0) | 536 ± 71(21) | 189 ± 87(82) |
| | T cells | 808 ± 33(0) | 647 ± 171(20) | 663 ± 18(18) |

[a] Control media (RPMI 1640) and supernatants of CEM-CM3 and 8E-24 were incubated with $2 \times 10^7$/ml T cells or B cells for 2 hours at 37° C. The cells were then removed by centrifugation.
[b] B cells were obtained by adherence to a nylon wool column. T cells were obtained by SRBC-rosette formation of the nylon wool nonadherent cells.
[c] Data are expressed as mean ± S.D. of triplicate samples. Percent suppression is given in parentheses.

TABLE 3
SUPPRESSION OF ANTIBODY PRODUCTION IN CULTURES REGULATED BY T4+ CELLS

| | T4+:B ratio[a] | IgM Production in 7 day Cultures, ng/culture | | |
|---|---|---|---|---|
| | | Medium Control | Supernatants (1:6 dilution) | |
| | | | CEM-CM3 | 8E-24 |
| Expt. I | 2:1 | 342 ± 42(0)[b] | 263 ± 70(23) | 97 ± 35(81) |
| | 5:1 | 637 ± 67(0) | 621 ± 224(3) | 663 ± 37(0) |
| Expt. II | 2:1 | 711 ± 54(0) | | 223 ± 37(69) |
| | 4:1 | 848 ± 25(0) | | 459 ± 100(46) |
| | 6:1 | 824 ± 58(0) | | 637 ± 147(23) |

[a] T4+ cells were isolated using a negative selection technique as described in Material and Methods. SRBC-rosette negative cells were used as the B cell enriched population. The numbers of B cells were fixed ($3 \times 10^4$/culture) and variable numbers of T4+ cells were added.
[b] Data are expressed as the mean ± S.D. of triplicate samples. Percent suppression is given in parentheses.

TABLE 4
ANALYSIS OF MOLECULAR SIZE OF HYBRIDOMA SUPPRESSOR FACTOR

| | Supernatant[a] Fractions | IgM Production in 7 day Cultures, ng/culture | |
|---|---|---|---|
| | | Medium Control | 8E-24 |
| Expt. I | Unfractionated | 212 ± 24(0)[b] | 86 ± 8(60) |
| | >10K | 209 ± 18(0) | 159 ± 33(24) |
| | <10K | 203 ± 48(0) | 92 ± 10(55) |
| Expt. II | Unfractionated | 280 ± 34(0) | 134 ± 7(52) |
| | >10K | 352 ± 26(0) | 259 ± 32(26) |

TABLE 4-continued

ANALYSIS OF MOLECULAR SIZE OF
HYBRIDOMA SUPPRESSOR FACTOR

| Supernatant[a] | IgM Production in 7 day Cultures, ng/culture | |
| --- | --- | --- |
| Fractions | Medium Control | 8E-24 |
| <10K | 293 ± 38(0) | 97 ± 14(67) |

[a]Control medium (RPMI 1640) and 8E-24 supernatant were separated into two fractions using a defined pore microconcentrator with an approximate pore size of 10,000 MW. Concentrated supernatants (5 × concentration) from the upper chamber were reconstituted with RPMI 1640 to the original volume and referred to as the >10K fraction. Filtered supernatants from the lower chamber are referred to as <10K fraction. Each of these fractions were added to the cultures at a 1:6 dilution.
[b]Data are expressed as mean ± S.D. of triplicate samples. Percent suppression is given in parentheses.

I claim:

1. A compound (suppressor factor) essentially free of compounds of molecular weight above 10,000, said compound characterized in that
   it is water soluble,
   it has a molecular weight between about 1,000 and 10,000,
   it suppresses immunoglobulin synthesis in pokeweed mitogen-stimulated human lymphocytes,
   it does not inhibit proliferation of human lymphocytes induced by concanavalin A or pokeweed mitogen,
   it inhibits phytohemmaglutinin-induced proliferation of human T4 cells, and
   it inhibits IL-2 production of human T4 cells.

* * * * *